US005756729A

United States Patent [19]

Khanna et al.

[11] Patent Number: 5,756,729
[45] Date of Patent: May 26, 1998

[54] PROCESS FOR THE MANUFACTURE OF 8-CHLORO-6 (2-FLUOROPHENYL)-1 METHYL-4H-IMIDAZO [1,5A] [1,4] BENZODIAZEPINE (MIDAZOLAM)

[75] Inventors: Jag Mohan Khanna; Naresh Kumar; Chandrahas Khanduri; Mukesh Kumar Sharma; Pankaj Sharma; Swargam Sathyanarayan; Girij Pal Singh, all of New Delhi, India

[73] Assignee: Ranbaxy Laboratories, Ltd., New Delhi, India

[21] Appl. No.: 728,808

[22] Filed: Oct. 9, 1996

[30] Foreign Application Priority Data

Jun. 13, 1996 [IN] India ........................ 1298/96

[51] Int. Cl.$^6$ ............ C07D 243/10; C07D 243/14; A61K 31/55
[52] U.S. Cl. .............. 540/557; 540/558; 540/553; 540/555; 514/220
[58] Field of Search ............ 514/220; 540/558, 540/557, 555

[56] References Cited

U.S. PATENT DOCUMENTS

| | | | |
|---|---|---|---|
| 4,005,099 | 1/1977 | Gall | 260/309 |
| 4,194,049 | 3/1980 | Field et al. | 548/336 |
| 4,226,771 | 10/1980 | Walser | 260/243.3 |
| 4,280,957 | 7/1981 | Walser et al. | 260/244.4 |
| 4,307,237 | 12/1981 | Walser et al. | 548/342 |

FOREIGN PATENT DOCUMENTS

| | | | |
|---|---|---|---|
| 0017181 | 10/1980 | European Pat. Off. | C07D 487/04 |
| 2537069 | 3/1976 | Germany | C07D 249/08 |
| 2540522 | 4/1976 | Germany | C07D 487/04 |
| 55-81862 | 6/1980 | Japan | C07D 233/58 |
| 1517165 | 7/1978 | United Kingdom | C07D 233/64 |

OTHER PUBLICATIONS

Fryer et al., J. Org. Chem., (1978), 43 (23), pp. 4480–4484.
Walser et al., J. Org. Chem. (1978), 43 (5), 936–44.
Walser et al., J. Heterocycl. Chem. (1983), 20 (3), 551–558.
Ramig et al., Tetrahederon Lett. (1992), 33 (42), pp. 6279–6282.

Primary Examiner—Johann Richter
Assistant Examiner—Sabiha N. Qazi
Attorney, Agent, or Firm—Meltzer, Lippe, Goldstein et al.

[57] ABSTRACT

A multistep process for producing 8-chloro-6-(2-fluorophenyl)-1-methyl-4-H-imidazo[1,5a][1,4] benzodiazepine (midazolam) comprises treating a compound of Formula II with a lower alkyl dithiol to produce a compound of Formula III, wherein n=2 or 3, converting the compound of Formula III to a compound of Formula VII, and then treating the compound of Formula VII with a deprotecting agent, thereby producing midazolam. Novel intermediate compounds are also disclosed.

24 Claims, No Drawings

PROCESS FOR THE MANUFACTURE OF 8-CHLORO-6 (2-FLUOROPHENYL)-1 METHYL-4H-IMIDAZO [1,5A] [ 1,4] BENZODIAZEPINE (MIDAZOLAM)

FIELD OF THE INVENTION

The present invention relates to a commercially viable manufacturing process for the anaesthetic midazolam, i.e., 8-chloro-6-(2-fluorophenyl)-1-methyl-4H-imidazo[1,5a] [1,4] benzodiazepine (I), which has the following structural formula:

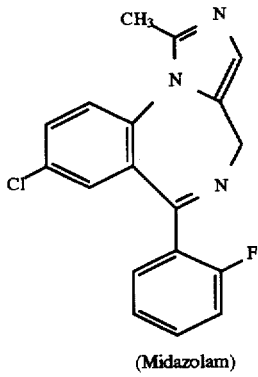

(Midazolam)

BACKGROUND OF THE INVENTION

Belgian Patent No. 839,364 (September 1976) describes the pharmaceutical utilities of imidazobenzodiazepines as sedatives, anxiolytics, muscle relaxants and anti-convulsant.

German Patent Specification DE 2,540,522 (April 1976) describes a process for the preparation of midazolam which process mainly comprises the treatment of the corresponding benzodiazepinone derivative with methylamine/titanium tetrachloride, followed by nitrosation and reaction with nitromethane to get the corresponding nitromethylene derivative. This compound is reduced with Raney Nickel and reacted with triethyl orthoacetate to get dihydro midazolam, which on dehydrogenation with manganese dioxide gives midazolam.

The U.S. Pat. Nos. 4,280,957 (March, 1981), 4,194,049 (March, 1980), and 4,226,771 (October, 1980) describe processes for the preparation of midazolam. The process according to U.S. Pat. No. 4,280,957 essentially comprises the same process for the manufacture of midazolam as is described in German Patent Specification DE 2,540,522.

The process according to U.S. Pat. No. 4,194,049 essentially comprises the preparation of midazolam by the deprotection of the corresponding imidazobenzodiazepine phthalimide derivative. This intermediate is produced by a multistep process starting from 4-chloro-2-[(2-flurorophenyl)methyl]benzenamine.

The process according to U.S. Pat. No. 4,226,771 essentially comprises the cyclization of the corresponding 2-carboxaldoxime derivative with acetaldehyde to give midazolam. The carboxaldoxime intermediate is produced in a five-step process starting from 2-amino-5-chloro-2'-fluorobenzophenone.

The said conventional processes for the preparation of midazolam involve tedious and complex chemistry, result in low yields, require time consuming cumbersome chromatographic separations and are consequently uneconomical for the preparation of midazolam on a commercial scale.

SUMMARY OF THE INVENTION

The present invention provides a novel multistep process for manufacturing midazolam which is economical, convenient to operate at commercial scale, and does not require chromatographic separations. Furthermore, the starting material is available on a commercial scale.

According to the present invention, midazolam is manufactured by the reaction sequence shown in the following scheme.

REACTION SCHEME

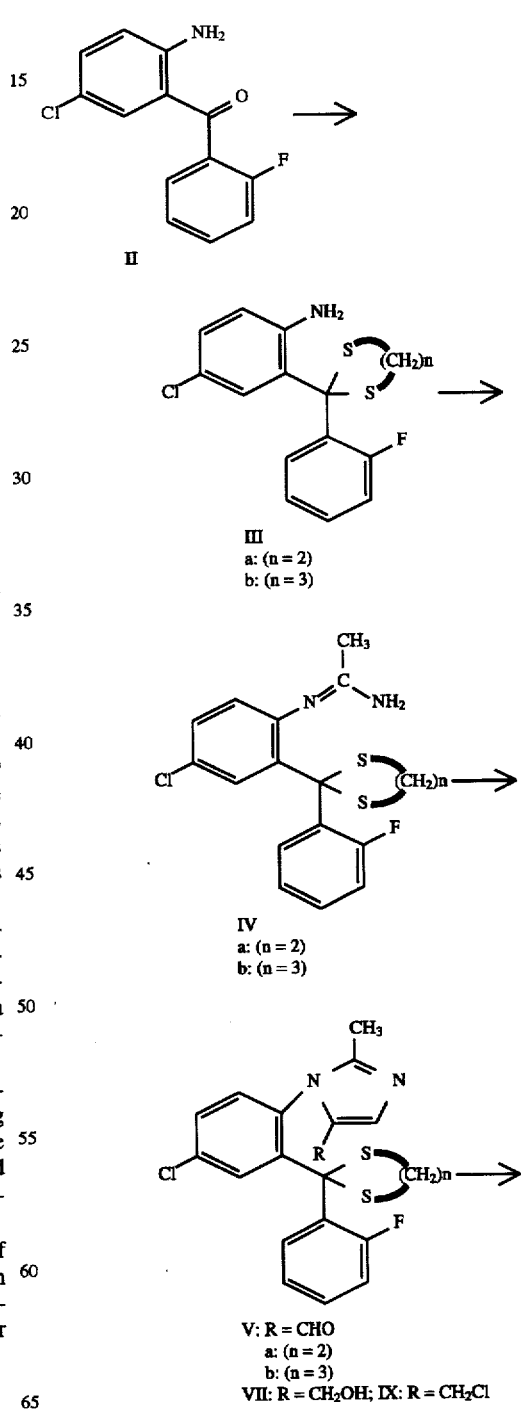

-continued
REACTION SCHEME

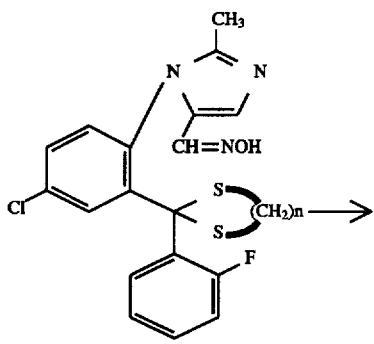

VI
a: (n = 2)
b: (n = 3)

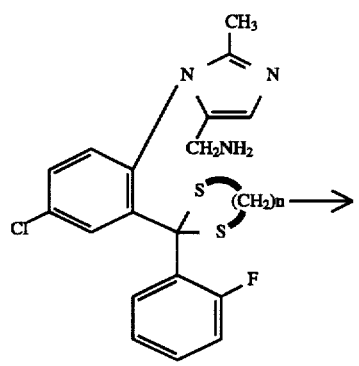

VII
a: (n = 2)
b: (n = 3)

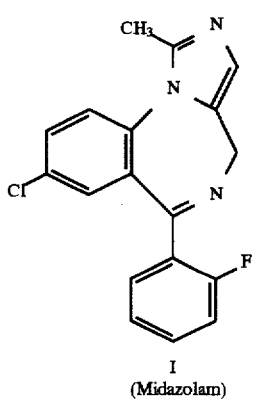

I
(Midazolam)

DETAILED DESCRIPTION OF THE INVENTION

In accordance with the present invention, midazolam is manufactured starting from commercially available 2-amino-5-chloro-2'-fluorobenzophenone (II). It is treated with 1,2-ethanedithiol or 1,3-propanedithiol in the presence of a Lewis acid such as aluminum chloride, zinc chloride, titanium tetrachloride, boron trifluoride, preferably, titanium tetrachloride. Suitable solvents for this reaction are halogenated solvents such as chloroform, dichloromethane or dichloroethane. The reaction temperature may vary from about −5° C. to about 90° C., preferably, in the range of about 40°–45° C. Suitable work-up of the reaction mixture gives the intermediate of structural formula-III, which is suitable for the next step without further purification.

The compound of structural formula-III is reacted with acetonitrile, in the presence of Lewis acids such as dry hydrogen chloride gas, aluminum chloride, boron trifluoride, zinc chloride or titanium tetrachloride, most preferably, aluminum chloride. The reaction temperature may vary from room temperature to reflux temperature. Preferably, the reaction is carried out at reflux. Work-up of the reaction mixture yields intermediate-IV which is sufficiently pure to use in the next step without further purification.

The compound of structural formula-IV, 4-chloro-2[2-(2-fluorophenyl)-1,3-dithiolan-2-yl]-N-(1-aminoethylidine) benzenamine is reacted with a halomalonaldehyde, such as bromomalonaldehyde, in an alcoholic solvent, such as a $C_1$–$C_4$ alcohol, preferably isopropyl alcohol, in the presence of triethylammonium acetate to give the compound of structural formula-V. The reaction temperature may vary from room temperature to reflux and is preferably carried out at the reflux temperature of the selected solvent.

The compound of formula-V is thereafter reacted with a hydroxylamine salt in alcoholic solvents such as $C_1$–$C_4$ alcohols at a temperature ranging from room temperature to reflux, preferably, at 45°–50° C., to yield the corresponding oxime compound (formula-VI) quantitatively and in a sufficiently pure form so that purification steps are not needed.

The compound of formula-VI is reduced to the aminomethyl derivative (VII) without affecting the other functionalities in the molecule. The preferred reducing agents for this reaction are metal hydrides such as lithium aluminum hydride, sodium borohydride, or sodium cyanoborohydride. A catalytic quantity of titanium trichloride and ammonium acetate may be added to the reaction mixture. The reaction temperature may vary from about −5° C. to about 40° C., and is preferably carried out at ambient temperature.

The deprotection of the compound of formula-VII gives midazolam. Reagents which may be used for this deprotection step include iodine/ dimethylsulfoxide, methyl iodide in methanol, cupric chloride/ cupric oxide in acetone, mercuric oxide/boron trifluoride in tetrahydrofuran and water, ceric ammonium nitrate in an organic solvent, and N-bromo succinimide in acetone, preferably, ceric ammonium nitrate in an organic solvent. The most preferred solvent for ceric ammonium nitrate is acetonitrile at ambient temperature. The reaction mixture on work-up gives midazolam which can be easily purified by crystallization.

Alternatively, compound of formula-VII may be obtained from compound-V by reduction using metal hydrides to produce compound-VIII which is then treated with thionyl chloride to give compound-IX followed by the amination of compound-IX using ammonia gas to produce compound-VII. Deprotection of compound-VII then proceeds as described above.

The following examples illustrate the present invention and as such are not to be considered as limiting the invention set forth in the claims appended hereto.

EXAMPLE-I

Preparation of 4-Chloro-2[2-(2-fluorophenyl)-1,3-dithiolan-2-yl]benzenamine (IIIa)

To a one litre three necked flask, fitted with a stirrer, reflux condenser and a dropping funnel, dichloroethane (300 ml) was added, followed by the addition of 2-amino-5-chloro-2'-fluorobenzophenone (II, 50 g, 0.2 mole), ethanedithiol (20.68 g, 0.22 mole), and titanium tetrachloride (75.6 g, 0.4 mole). The reaction mixture was stirred at 52°–55° C. for 8 hrs and then 300 ml of water was added and stirred at ambient temperature for 30 minutes. The precipitated solid was filtered, washed with water and dried. Crude product was obtained as an off-white solid (50 g). An analytical sample prepared by crystallization from dichloroethane had a melting point of 199°–195° C.; NMR (CDCl$_3$, 200 MHz): δ 3.4 (m, 2H, S-CH$_2$), 3.6 (m, 2H, S-CH$_2$), 3.7 (s, 2H, NH$_2$), 7.0–8.0 (m, 7H, aromatic H); IR (KBr): 3390, 1500, 1220, 780 cm$^{-1}$.

EXAMPLE-II

Preparation of 4-Chloro-2[2-(2-fluorophenyl)-1,3-dithiane-2-yl]benzenamine (IIIb)

The compound IIIb was obtained from compound II and propanedithiol following the same process substantially as described for compound IIIa. Compound IIIb was obtained as white to pale yellow crystals having a melting point of 135°–136° C.; NMR (CDCl$_3$, 200 MHz): δ 2.04–2.11 (m, 2H, CH$_2$), 3.8 (s, 2H, NH$_2$), 6.5–7.9 (m, 7H, aromatic H); IR (KBr): 4310, 3440, 1640, 1490, 1400, 1300, 1210, 1180, 780, 640 cm$^{-1}$.

EXAMPLE-III

Preparation of 4-Chloro-2[2-fluorophenyl)-1,3-dithiane-2-yl]-N-(1-aminoethylidene) benzenamine (IVa)

To a 250 ml three-necked flask fitted with a thermometer pocket and a reflux condenser, and containing 89 ml of acetonitrile, 4-chloro-2[2-(2-fluorophenyl)-1,3-dithiolan-2-yl]benzenamine (IIIa, 32 g, 0.1 mole) was added. To this stirred suspension, aluminum chloride (26.19 g, 0.2 mole) was added carefully at ambient temperature in 10 minutes. It was then refluxed for two days and cooled to ambient temperature. The reaction mixture was poured to cold water (300 ml) at 10°–15° C. This was basified with aqueous sodium hydroxide solution (20%) and the product was extracted with ethyl acetate (2×150 ml). Solvent was recovered under vacuum at 35°–40° C. to obtain an off-white solid (24.5 g). An analytical sample, prepared by crystallization from a mixture of toluene and hexane had a melting point of 189°–190° C.; NMR (CDCl$_3$ 200 MHz): δ 2.28 (m, 3H, CH$_3$), 3.26 (s, 4H, S-CH$_2$-CH$_2$-CH$_2$-S), 4.3 (br-s, 2H, NH$_2$, D$_2$O exchangeable), 6.3–8.1 (m, 7H, aromatic H); IR (KRr): 3495, 1650, 1480, 1390, 1210, 1100, 820, 780 cm$^{-1}$.

EXAMPLE-IV

Preparation of 4-Chloro-2[2-fluorophenyl) -1,3-dithiane-2-yl]-N-(1-aminoethylidene) benzenamine (IVb)

Compound IVb was obtained as an off-white solid from compound IIIb and acetonitrile by following a process analogous to that for producing compound IVa. The product collected had a melting point of 163°–165° C.; NMR (CDCl$_3$ 200 MHz): δ 1.53 (s, 3H CH$_3$) 2.01–2.09 (m, 2H, CH$_2$), 2.9 (m, 4H, 2xs-CH$_2$), 3.9 (br-s, 2H, NH$_2$), 6.58–8.22 (m, 7H, aromatic H); IR (KRr): 3510, 3480, 1640, 1420, 1380, 1180, 815, 780 cm$^{-1}$.

EXAMPLE-V

Preparation of 1-[4-Chloro-2{2-(2-fluorophenyl)1,3-dithiolan-2-yl}phenyl]-2-methyl-1H-imidazole-5-carboxaldehyde (Va)

To a 500 ml three necked flask containing isopropyl alcohol (123 ml) was added 4-chloro-2[2-(2-fluorophenyl)-1,3-dithiolan-2-yl]-N-(1-aminoethylidene) benzenamine (IVa, 20 g, 0.054 mole), followed by the addition of acetic acid and triethylamine (1.1 molar equivalent of each). A solution of bromomalonaldehyde (8.65 g, 0.055 mole) in 100 ml of isopropyl alcohol was added and refluxed for 6 hrs. The mixture was concentrated under vacuum at 35°–40° C. and the residue treated with water (200 ml), followed by extraction with dichloromethane (100 ml). The organic layer was concentrated and the product isolated. The crude product (19.2 g) was obtained as a yellowish, off-white solid having a melting point of 143°–144° C.; NMR (CDCl$_3$ 200 MHz): δ 194 (s, 3H, CH$_3$) 3.21–3.39 (m, 4H, S-CH$_2$-CH$_2$-S), 6.9-8.3 (m, 8H, aromatic H), 9.16 (s, 1H, —CHO); IR (KBr): 1680, 1465, 1250, 1390, 810, 780 cm$^{-1}$.

EXAMPLE-VI

Preparation of 1-[4-Chloro-2{2-(2-fluorophenyl)1,3-dithiane-2-yl}phenyl]-2-methyl-1H-imidazole-5-carboxaldehyde (Vb)

Compound Vb was prepared from compound IVb and bromomalonaldehyde by using a process analogous to that for compound Va. Compound Vb had a melting point of 193°–194° C.; NMR (CDCl$_3$, 200 MHz): δ 1.88 (s, 3H, CH$_3$), 1.91–1.96 (m, 2H, CH$_2$), 2.71–2.92 (m, 4H, 2xs-CH$_2$), 6.93–8.31 (m, 8H aromatic H), 9.17 (s, 1H, CHO); IR (KBr): 1680, 1485, 1190, 820, 780 cm$^{-1}$.

EXAMPLE-VII

Preparation of 1-[4-Chloro-2{2-(2-fluorophenyl)1,3-dithiolan-2-yl}phenyl]-2-methyl-1]-1H-imidazole-5-carboxaldoxime (VIa)

To a 100 ml three-necked flask containing 4-chloro-1-[2{2-(2-fluorophenyl)-1,3-dithiolan-2-yl}phenyl]-2-methyl-1H-imidazole-5-carboxaldehyde (Va, 4 g, 0.0095 mole) alcohol (4 ml) was added, followed by the addition of hydroxylamine hydrochloride (1.05 molar equivalent). The mixture was stirred at ambient temperature for 30 minutes. Solvent was completely recovered under vacuum, treated with water (50 ml), and was made alkaline using aqueous sodium bicarbonate solution. The precipitated solid was filtered, washed with water and dried yielding product (4 g) having a melting point of 243°–244° C.; NMR (CDCl$_3$ 200 MHz): δ 2.1 (s, 3H, CH$_3$), 3.17–3.37 (m, 4H, S-CH$_2$-CH$_2$-S), 6.5 (s, 1H=C-H), 6.7–8.2 (m, 8H, aromatic-H), 8.5 (br-s, 1H-NOH); IR (KBr): 1430, 1190, 1100, 985, 820, 780 cm$^{-1}$.

EXAMPLE-VIII

Preparation of 1-[4-Chloro-{2-(2-fluorophenyl)1,3-dithiane-2yl}phenyl]-2-methyl-1]-1H-imidazole-5-carboxaldoxime (VIb)

The compound VIb was obtained as an off-white powder from compound Vb and hydroxylamine hydrochloride by a process analogous to that for the preparation of compound VIa. NMR (CDCl$_3$, 200 MHz): δ 1.98 (s, 3H, CH$_3$), 2.07 (s, 2H, CH$_2$), 2.78 (s, 4H, 2xsCH$_2$), 6.69 (s, 1H, HC=), 6.89–8.18 (m, 8H, aromatic-H); IR (KBr): 3010, 3080, 1500, 1410, 1170, 990, 970, 830, 785 cm$^{-1}$.

EXAMPLE-IX

Preparation of 5-Aminomethyl-1[4-chloro-2{2-(2-fluorophenyl)1,3-dithiolan-2-yl}phenyl]-2-methyl-1H-imidazole (VIIa)

The aldoxime of formula VIa (4 g, 0.093 mole) was stirred in methanol (40 ml) and to this was added ammonium acetate (7.8 g) followed by the addition of sodium cyanoborohydride (1.7 g, 3 molar equivalent) at ambient temperature. To this was added titanium trichloride aqueous solution (15%, 20.8 ml) in about 15 minutes. The mixture was stirred for 12 hrs. at ambient temperature. The reaction mixture was made alkaline by the addition of ammonia and then extracted with ethyl acetate (2×50 ml). On complete recovery of the solvent, 3.2 g of compound VIIa having a melting point of 230° C. (decomp) was collected. NMR ($CD_3OD$, 200 MHz): δ 1.91 (s, 3H, $CH_3$); 3.2–3.4 (m, 4H, $S-CH_2-CH_2-S$), 3.45–3.51 (m, 2H, $CH_2$, $CH_2N$), 3.88 (s, 2H, $NH_2$), 7.02–7.93 (m, 8H, aromatic-H); IR (KBr): 3410, 1590, 1510, 1410, 1180, 820, 780, 640 $cm^{-1}$.

EXAMPLE-X

Preparation of 5-Aminomethyl-1[4-chloro-2{2-(2-fluorophenyl) 1,3-dithiane-2-yl}phenyl]-2-methyl-1H-imidazole (VIIb)

The compound VIIb was prepared by the reduction of compound VIb with sodium cyanoborohydride as off-white crystals by following a process analogous to that for the preparation of compound VIIa. The product showed NMR ($CDCl_3$, 200 MHz): δ 1.5–1.9 (m, 2H, $CH_2$), 2.1 (s, 3H, $CH_3$), 2.72–2.82 (m, 4H, 2×$SCH_2$), 3.4–3.6 (dd, 2H, $CH_2N$), 6.77–7.85 (m, 8H, aromatic-H); IR ($CHCl_3$): 3400, 1490, 1380, 1240, 1160, 980, 760 $cm^{-1}$.

EXAMPLE-XI

Preparation of 5-Hydroxymethyl-1[4-chloro-2{2-(2-fluorophenyl)1,3-dithiolan-2-yl}phenyl]-2-methyl-1H-imidazole (VIII)

The compound of formula Va (5 gm) was dissolved in methanol (70 ml) and cooled to 5°–7° C. To this was added sodium borohydride (1.75 gm, 2 molar equivalent) portionwise at 10°–15° C. and stirred for 20 minutes. To this was added acetic acid (2.9 gm,). Solvent was recovered completely at 40°–42° C. under vacuum, and cold water (65 ml) was added. The mixture was stirred for 15 minutes at ambient temperature and the solid was filtered, washed with water and dried. The yield was 4.23 gm with a melting point of 236°–240° C.; NMR ($CDCl_3$, 200 MHz) δ: 1.94 (s, 3H, $CH_3$), 2.9 (s, 1H OH), 3.12–3.3 (m, 4H, $S-CH_2-CH_2-S$), 4.02–4.29 (dd, 2H, $CH_2-OH$) 6.8–7.8 (m, 8H, aromatic-H); IR (KBr): 3250, 1470, 1200, 1010, 780 $cm^{-1}$.

EXAMPLE-XII

Preparation of 5-Chloromethyl-1[4-chloro-2{2-(2-fluorophenyl)1,3-dithiolan-2-yl}phenyl]-2-methyl-1H-imidazole IX The hydroxy derivative of formula VIII (4 gm) was stirred in 20 ml of chloroform at 0° to 5° C. and to this was added thionyl chloride (2.5 gm) and stirred at 5°–10° C. for 30 minutes, and then for 1 hr. at 20°–25° C. Chloroform was recovered completely and to this was added 20 ml of THF. The precipitated solid was filtered under nitrogen atmosphere and washed well with THF (20 ml). The title compound was obtained as an off-white powder (4.6 gm) as its hydrochloride. Melting point 147°–150° C.; NMR (DMSO, 200 MHz): δ 2.19 (S, 3H, $CH_3$), 3.2–3.5 (m, 4H, $S-CH_2 \times CH_2-S$), 4.5–4.9 (dd, 2H, $CH_2,Cl$) 7.19–8.34 (m, 3H, aromatic-H); IR (KBr): 3500, 1610, 1480, 1100, 780 $cm^{-1}$.

EXAMPLE-XIII

Preparation of 5-Aminomethyl-1[4-chloro-2{2-(2-fluorophenyl)1,3-dithiolan-2-yl}phenyl]-2-methyl-1H-imidazole (VIIa)

Compound IX (2 gm) and sodium iodide (0.1 gm) were suspended in 30 ml of chloroform at 0°–2° C. and dry ammonia gas was purged for 3 hrs. The solvent was completely recovered under vacuum. Residue thus obtained was crystallized by ethyl acetate (5 ml), giving 0.8 gm of amino compound of formula-VIIa having a melting point of 230° C. (decomp).

EXAMPLE-XIV

Preparation of 8-Chloro-6-(2-fluorophenyl)-1-methyl-4H-imidazol[1, 5a] [1,4] benzodiazepine (Midazolam)

5-Aminomethyl-1 [4-chloro-2{2- (2-fluorophenyl) 1,3-dithiolan-2-yl}phenyl]-2-methyl-1H-imidazole (VIIa, 3.2 g, 0.0073 mole) was dissolved in a mixture of acetonitrile and water (5:1, 108 ml). To this was added ceric ammonium nitrate (16.5 g, 4 molar equivalent) and stirred for 10 hrs. at ambient temperature. Solvent was recovered under vacuum at 25°–30° C. and made alkaline by the addition of ammonia. The mixture was extracted with ethyl acetate (50 ml) and crude product (2 gm) was obtained by the recovery of solvent under vacuum. The residue was purified by crystallization. Melting point: 161°–162° C.

EXAMPLE-XV

Preparation of 8-Chloro-6-(2-fluorophenyl)-1-methyl-4H-imidazol[1, 5a] [1,4] benzodiazepine (Midazolam)

Mercuric oxide (1 gm) was added to a stirred mixture of THF and water (8.5 ml and 1.5 ml) followed by addition of $BF_3$-etherate (0.6 ml). Mixture was stirred at ambient temperature and to this was added a solution of 5-aminomethyl-1[4-chloro-2{2-(2-fluorophenyl)1,3-dithiolan-2-yl}phenyl]-2-methyl-1H-imidazole (VIIa) in 10 ml of THF. Mixture was stirred for 10 hrs. at ambient temperature and slowly heated 50°–55° C. It was further stirred for 5 hrs. at this temperature, poured to water, basified with ammonia solution and extracted with ethyl acetate (2×30 ml). Residue obtained after the ethyl acetate recovery was purified by passing through a silica gel column and eluting with chloroform and acetone gradient. Melting point 161°–162° C.

EXAMPLE-XVI

Preparation of 8-Chloro-6-(2-fluorophenyl)-1-methyl-4H-imidazol[1, 5a] [1,4] benzodiazepine (Midazolam)

The title compound was obtained as a white crystalline solid from 5-aminomethyl-1[4-chloro-2{2-(2-fluorophenyl) 1,3-dithiane-2-yl}phenyl]-2-methyl-1H-imidazole (VIIb, 0.6 g) and ceric ammonium nitrate (3.0 g) in 20% aqueous acetonitrile following the same procedure as described in Example-XIV.

While the invention has been described by reference to specific embodiments, this was for purposes of illustration only. Numerous alternative embodiments will be apparent to those skilled in the art and are considered to be within the scope of the invention.

We claim:
1. A process for making a compound of formula I:

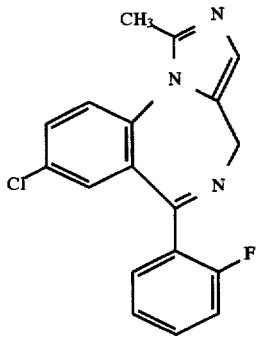

which comprises (i) treating a compound of formula II:

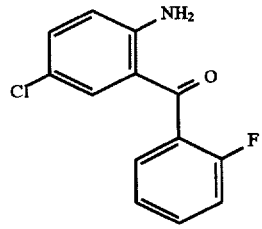

with a lower alkyl dithiol to produce a compound of formula III:

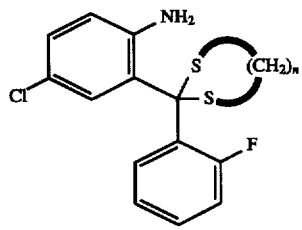

wherein n=2 or 3;

(ii) treating said compound of formula III with acetonitrile to produce a compound of formula IV:

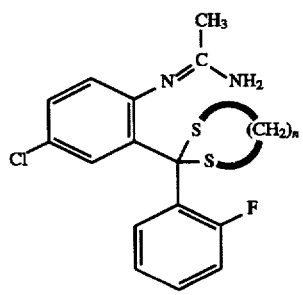

(iii) treating said compound of formula IV with a halomalonaldehyde to produce a compound of formula V:

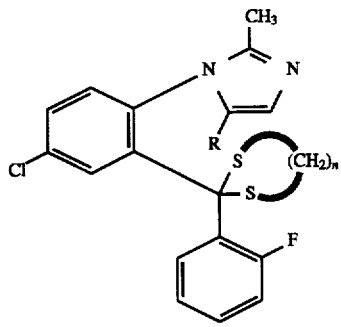

wherein R is the group CHO;

(iv) treating the compound of formula V with a hydroxylamine salt to produce a compound of formula VI:

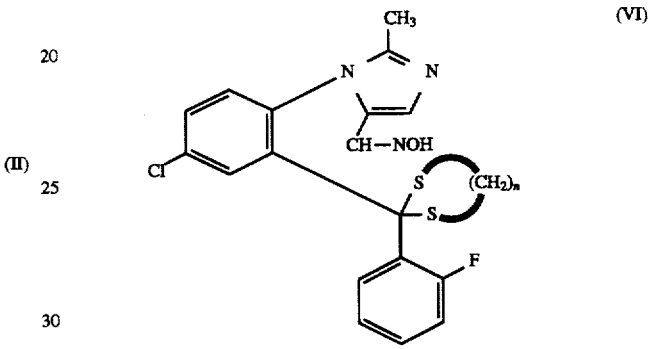

(v) treating said compound of formula VI with a reducing agent to produce a compound of formula VII:

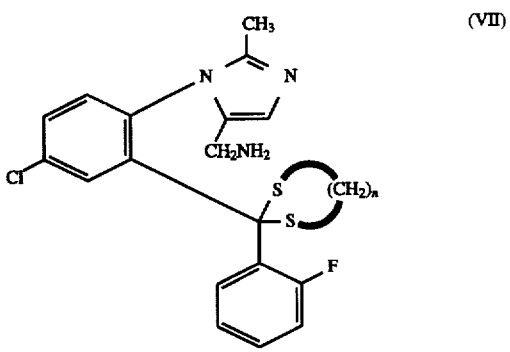

(vi) treating said compound of formula VII with a deprotecting agent, thereby to produce said compound of formula I.

2. The process of claim 1 wherein said lower alkyl dithiol of step (i) is 1,3-propanedithiol or 1,2-ethanedithiol.

3. The process of claim 2 wherein the reaction of step (i) is carried out in the presence of a Lewis acid.

4. The process of claim 3 wherein said Lewis acid is titanium tetrachloride, aluminum chloride, zinc chloride, or boron trifluoride.

5. The process of claim 1 wherein the reaction of step (ii) is carried out in the presence of a Lewis acid.

6. The process of claim 5 wherein said Lewis acid is titanium tetrachloride, aluminum chloride, boron trifluoride, zinc chloride, or dry hydrogen gas.

7. The process of claim 1 wherein said halomalonaldehyde is bromomalonaldehyde.

8. The process of claim 7 wherein the reaction of step (iii) is carried out in a $C_1$–$C_4$ alcoholic solvent.

9. The process of claim 1 wherein said hydroxylamine salt of step (iv) is hydroxylamine hydrochloride.

10. The process of claim 9 wherein the reaction of step (iv) is carried out in a $C_1$–$C_4$ alcoholic solvent.

11. The process of claim 1 wherein said reducing agent of step (v) is an alkali metal hydride.

12. The process of claim 11 wherein said alkali metal hydride is sodium borohydride, sodium cyanoborohydride, or lithium aluminum hydride.

13. The process of claim 1 wherein said deprotecting agent of step (vi) is iodine, methyl iodide, cupric chloride, cupric oxide, mercuric oxide, boron triflouride, ceric ammonium nitrate, N-bromo succinimide, or combinations thereof.

14. The process of claim 13 wherein said deprotecting agent is mercuric oxide or ceric ammonium nitrate.

15. A process for making a compound of formula I:

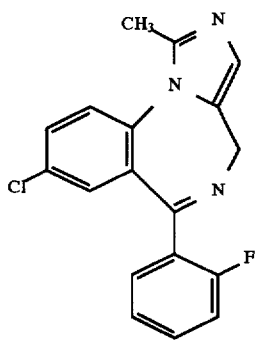

which comprises:

(i) treating a compound of formula II:

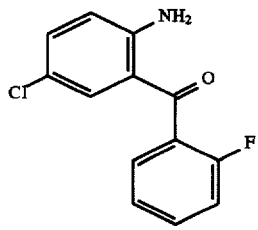

with a lower alkyl dithiol to produce a compound of formula III:

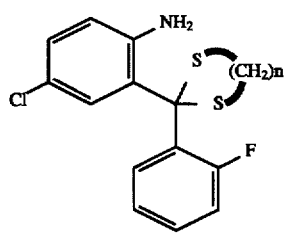

wherein n=2 or 3;

(ii) treating said compound of formula III with acetonitrile to produce a compound of formula IV:

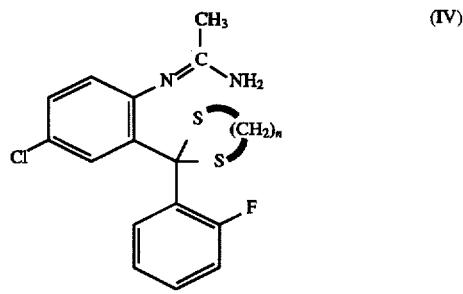

(iii) treating said compound of formula IV with a halomalonaldehyde to produce a compound of formula V:

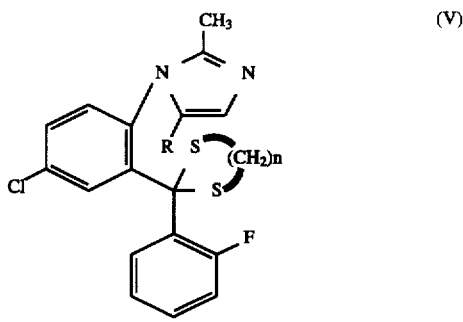

wherein R is the group CHO;

(iv) treating said compound of formula V with a reducing agent to produce a compound of formula VIII:

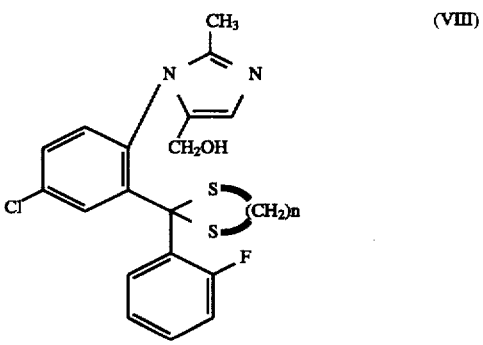

(v) treating said compound of formula VIII with a halogenating agent to produce a compound of formula IX:

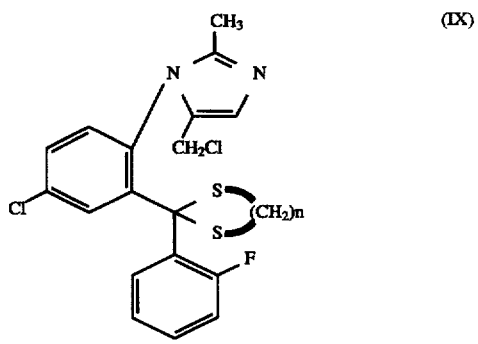

wherein X is a halo group;

(vi) treating said compound of formula IX with an aminating agent to produce a compound of formula VII:

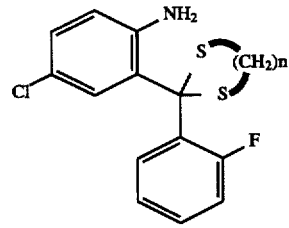
(III)

wherein n=2 or 3; converting said compound of formula III to a compound of formula VII:

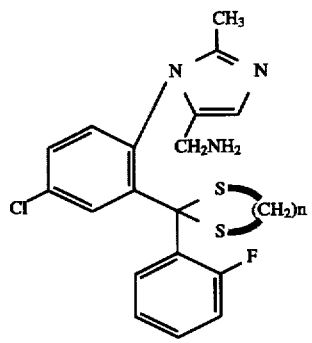
(VII)

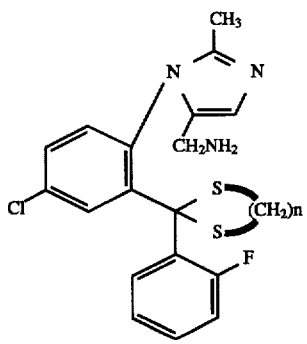
(VII)

(vii) and treating said compound of formula VII with a deprotecting agent, thereby to produce said compound of formula I.

16. The process of claim 15 wherein said reducing agent of step (iv) is an alkali metal hydride.

17. The process of claim 16 wherein said alkali metal hydride is sodium borohydride.

18. The process of claim 15 wherein X is a chloro group.

19. The process of claim 18 wherein said halogenating agent is thionyl chloride.

20. The process of claim 15 wherein said aminating agent of step (VI) is gaseous ammonia.

21. A process for producing a compound of formula I:

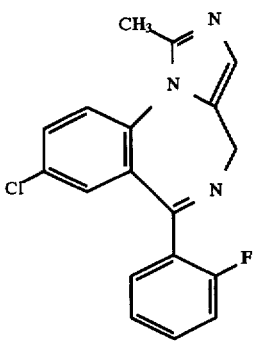
(I)

which comprises treating a compound of formula II:

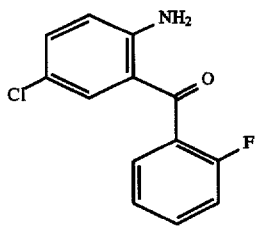
(II)

with a lower alkyl dithiol to produce a compound of formula III:

and treating said compound of formula VII with a deprotecting agent, thereby to produce said compound of formula I.

22. The process of claim 21 wherein said lower alkyl dithiol is 1,3-propane dithiol or 1,2-ethanedithiol.

23. The process of claim 21 wherein said deprotecting agent is iodine, methyl iodide, cupric chloride, cupric oxide, mercuric oxide, boron trifluoride, ceric ammonium nitrate, N-bromo succinimide, or combinations thereof.

24. The process of claim 21 wherein said deprotecting agent is mercuric oxide or ceric ammonium nitrate.

* * * * *